United States Patent [19]

Siggaard-Andersen

[11] 4,308,029

[45] Dec. 29, 1981

[54] METHOD AND CAPILLARY TUBE FOR TREATING BLOOD SAMPLE

[75] Inventor: Ole Siggaard-Andersen, Charlottenlund, Denmark

[73] Assignee: Radiometer A/S, Copenhagen, Denmark

[21] Appl. No.: 147,261

[22] Filed: May 5, 1980

Related U.S. Application Data

[63] Continuation of Ser. No. 973,815, Dec. 28, 1979, abandoned, which is a continuation of Ser. No. 843,211, Oct. 18, 1977, abandoned.

[30] Foreign Application Priority Data

Oct. 18, 1976 [DK] Denmark .............................. 4691/76

[51] Int. Cl.³ ...................... G01N 33/72; G01N 33/52
[52] U.S. Cl. ................... 23/230 B; 23/913; 356/40; 422/57; 422/58
[58] Field of Search ........................ 23/230 B; 422/57

[56] References Cited

U.S. PATENT DOCUMENTS

| 3,898,982 | 8/1975 | Katsuda | 128/2 F |
| 3,926,521 | 12/1975 | Ginzel | 128/2 F |
| 3,964,865 | 6/1976 | Das | 23/230 B |

OTHER PUBLICATIONS

"Gradwohl's Clinical Laboratory Methods," S. Frankel et al., eds., 7th Edition, 396–399, C. V. Mosby Co., Saint Louis, 1970.

*Primary Examiner*—Sidney Marantz
*Attorney, Agent, or Firm*—Hubbell, Cohen, Stiefel & Gross

[57] ABSTRACT

Deoxygenation of a blood sample prior to determination of carbon monoxide hemoglobin is performed in a capillary tube containing a dry reducing agent. Ready for use capillary tubes having long storage life contain dry reducing agent and are sealed at both ends. Preferred capillary tubes contain mixture of reducing agent, pH buffer and anticoagulating agent present as a dry material on the interior tube wall.

12 Claims, 1 Drawing Figure

U.S. Patent      Dec. 29, 1981      4,308,029
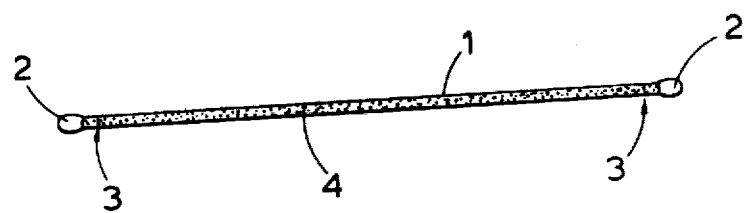

METHOD AND CAPILLARY TUBE FOR TREATING BLOOD SAMPLE

This is a continuation, of application Ser. No. 973,815, filed Dec. 28, 1979, abandoned, which is a continuation of application Ser. No. 843,211 filed Oct. 18, 1977, abandoned.

FIELD OF THE INVENTION

The present invention concerns a method for deoxygenating a blood sample and a capillary tube for use in the method.

BACKGROUND OF THE INVENTION

In the examination of patients for content of carbon monoxide hemoglobin (HbCO) in their blood, a blood sample is withdrawn, and the content of HbCO in the sample is determined with a spectrophotometer. This may be done either directly without pre-treatment of the blood sample or, to obtain a more exact determination, subsequent to removal of the oxygen content of the blood sample. The oxygen content of the blood sample may be removed by evacuation, venting with non-oxygenous gasses or by means of a reducing agent. A suitable reducing agent which may be used comprises an aqueous solution of sodium dithionate ($Na_2S_2O_4$) and tris(hydroxymethyl)-aminomethane ($C_4H_{11}NO_3$, in the following is designated Tris) in a concentration corresponding to about 5 times the stoichiometric amount when the solution of the reducing agent is added to the blood in the ratio 1:1 (v/v).

The reaction which proceeds when the oxygen content of the blood is reduced with dithionite appears from the below reaction scheme:

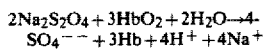

The spectrophotometric determination may be performed using a suitable photometer which is commercially available. An example of such photometer is described in U.S. Pat. No. 3,972,614. This photometer measures at a wave length of 506 nm and 600 nm. At 506 nm, hemoglobin, oxyhemoglobin ($HbO_2$) and carbon monoxide hemoglobin absorb to substantially the same extent, whereas, at 600 nm, there is a considerable difference between on the one hand the absorption by hemoglobin and on the other hand the absorption by oxyhemoglobin+carbon monoxide hemoglobin, the two latter absorbing to substantially the same extent at this wave length. When the blood sample is free of oxyhemoglobin, the content of carbon monoxide hemoglobin in the blood sample may be determined from these two measurements.

The execution of the above methods for preparing the blood sample for the spectrophotometric measurements is time-consuming and laborious. This may be illustrated by the following description of a method for reducing a blood sample using the above reducing agent:

(a) Centrifuge 10 ml of blood at 5000 r.p.m. for 3 minutes.
(b) Remove plasma by suction.
(c) Weigh out 31 mg of sodium dithionite and 22 mg Tris and dissolve in 5 ml of water. This is the reducing agent.
(d) Immediately transfer 2.5 ml of reducing agent to a glass syringe.
(e) Suction 2.5 ml of blood concentrate into the syringe, seal the syringe, mix the contents carefully and keep the syringe under rotation for 5–8 minutes.
(f) Measure MbCO content under anaerobic conditions.

As will appear from the above, this procedure is time and labor consuming it, involves possibility of errors and inaccuracies and it requires a relatively large amount of blood.

In Clin. Chim. Acta, 42 (1972), 85–100 and 101–108, a modification of the above-described process is disclosed in which the centrifugation of the blood is performed in a capillary tube and the resulting packed erythrocytes are transferred into a capillary tube into which an equal volume of the reducing agent is introduced from the glass syringe, the capillary tube is closed with plasticine, and mixing is accomplished by magnetic stirring by means of a metal stirrer provided in the tube and a magnet outside the tube. Although this method avoids the use of relatively large amounts of blood, the other measures are the same as set out in detail above, with the inherent disadvantages with respect to time- and labor consumption, the necessity of daily fresh preparation of the reducing agent, etc.

SUMMARY OF THE INVENTION

The present invention provides a novel and convenient method for deoxygenating a blood sample. The method permits a much simpler procedure in the determination of the content of carbon monoxide hemoglobin in the blood and other determinations in which a deoxygenated blood sample is to be used, for example in the zero-calibration of an oxygen saturation meter. In the method of the invention, the reduction of oxygen may be performed without dilution of the sample. The method of the invention comprises introducing the blood sample into a capillary tube which contains a dry reducing agent for the oxygen content of the blood, and allowing action of the reducing agent on the blood sample to take place in the capillary tube.

This provides an important simplification of the preparation of the blood for the photometric determination, and a number of factors of uncertainty are eliminated. As the reducing agent is present in the capillary tube in dry form, dilution of the whole blood sample is avoided, and therefore, in contrast to the above-mentioned known method, it is possible to determine the original hemoglobin concentration (in other words, the sum of all hemoglobin fractions). Furthermore, it is a widely used sample withdrawal technique to withdraw the blood from the patient in a capillary tube. Thus, this simple and well-established technique may, without any modification be used for introducing the whole blood in the specially prepared capillary tube used in the method of the present invention. In performing the method of the invention, it is suitable to fill up the capillary tube completely with the blood sample and thereafter seal the tube at both ends and then to mix the blood sample and the reducing agent in the capillary tube by means of a ferromagnetic body arranged in the capillary tube, for example a small piece of steel wire, which is moved by means of a magnet outside the tube. Subsequent to the reduction, the sample may be used for the purpose desired, for example for measurement of carbon monoxide hemoglobin, since it is easy and simple to directly transfer the sample to a photometer under anaerobic conditions.

The invention also relates to a capillary tube for use in the above method. The capillary tube contains a dry reducing agent for reduction of the oxygen content of the blood in a sufficient amount for reduction of the oxygen content in the volume of blood which can be contained in the capillary tube.

When the capillary tube is to be used for reduction of blood samples withdrawn directly from the patient, it should contain an anticoagulation agent in addition to the reducing agent. In the cases where the blood sample to be introduced in the capillary tube, for example from a syringe, has already been admixed with an anticoagulation agent, the anticoagulation agent can be omitted in the capillary tube. Suitably, the capillary tube of the invention is provided with the reducing agent and the possible anticoagulation agent and air-tightly sealed at both ends by a manufacturer, and in this form, the capillary tube can be stored for long periods with retention of its activity. This avoids the necessity of the user handling chemicals for the deoxygenation.

A suitable size of the capillary tube is a length of about 10 cm and a volume of about 100 microliters and it is preferred that the reducing agent and the optional additional reagents are applied as a layer of dry solid material on the interior tube wall. This may, for example, be obtained through the process described below.

The reducing agent in the capillary tube according to the invention is suitably dithionite, especially sodium dithionite, preferably combined with a suitable pH buffer, for example Tris. The amount of sodium dithionite in a capillary tube having a volume of 100 microliters is suitably at least 0.12 mg (the stoichiometric amount), preferably about 0.6 mg. The amount of Tris in the capillary tube is preferably 0.7 mg per mg of sodium dithionite.

When the capillary tube contains an anticoagulating agent, this is suitably applied to the interior wall of the capillary tube in a sufficient amount together with the reducing agent. Examples of anticoagulating agents suitable for this purpose are heparin or calcium binders such as trisodium citrate, disodium salt of ethylenediamine-tetraacetic acid, sodium fluoride or alkali metal salts of oxalic acid.

The prepared capillary tube of the invention is suitably made by passing a solution or suspension of a reducing agent in a volatile medium through a capillary tube under an oxygen-free atmosphere and allowing the solvent to evaporate to leave a layer of reducing agent on the interior wall of the capillary tube. When the reducing agent is sodium dithionite, this process may suitably be performed by passing a suspension of sodium dithionite and Tris in a volatile non-solvent for sodium dithionite and Tris through a capillary tube under an atmosphere free of oxygen and water vapor, suitably by dipping the lower end of the capillary tube into the suspension, whereby a liquid string is drawn into the capillary tube by the capillary forces, and thereafter, by means of applied reduced pressure, suctioning the liquid string to the other end of the capillary tube, the liquid medium evaporating during the suctioning. The capillary tube thus prepared should be kept under an inert atmosphere until it is sealed at both ends. The sealing may for example be a stopper of epoxy resin at each end of the capillary tube. Alternatively, the prepared capillary tube may be transferred, under an inert atmosphere, to an air-tight packing such as a laminated plastic-/aluminum bag.

As mentioned above, in addition to the reducing agent and the buffer which is optionally used together with the reducing agent, the capillary tube may contain an anticoagulating agent, and if an anticoagulating agent is included, it is suitably applied to the interior wall of the capillary tube together with the reducing agent in the manner described above. Alternatively, the reducing agent may, in the manner described above, be applied on the interior wall of a capillary tube which has already been treated with an anticoagulating agent. Capillary tubes prepared with heparin are known and commercially available (obtainable for example from Radiometer A/S, Copenhagen), and they may be prepared as described below. However, there may also be cases where the capillary tube is to be used in connection with blood samples already admixed with an anticoagulating agent, and in such case, the capillary tube need not be prepared with an anticoagulating agent. In a case where a capillary tube not prepared with anticoagulating agent is to be used for a directly withdrawn blood sample, it is also contemplated to add an anticoagulating agent immediately subsequent to opening the prepared capillary tube, or to introduce anticoagulating agents together with the stirrer body, possibly initially applied to the stirrer body.

As mentioned above, it is known to heparin-prepare glass capillary tubes for use in blood sample withdrawal to prevent the coagulation of the blood in the tubes. In such prepared glass capillary tubes, the heparin is present as a thin layer on the interior wall of the tube, and the procedure for applying this layer resembles the above-described process for preparing the capillary tube according to the invention; for example, a drop of a solution of 0.35 g sodium heparinate in 185 ml methanol containing 3.75 ml water is introduced, by means of a syringe with applied cannula, into one end of a capillary tube, whereafter the tube is kept for about 10 seconds in a heat chamber at about 70° C., whereafter cold air is blown through for about 10 seconds. The preparation of glass capillary tubes with a dry reducing agent for the oxygen content of blood and the subsequent sealing of the tube for obtaining a storable, easily handled aid for the deoxygenation of a blood sample is, in contrast, believed to be novel, and also the dry compositions comprising a reducing agent, for example dithionite, together with anticoagulants, for example heparin, ethylenediamine-tetraacetic acid and salts thereof, sodium citrate, sodium fluoride, etc., are believed to be novel.

BRIEF DESCRIPTION OF THE DRAWING

The drawing shows a capillary tube according to the invention.

DESCRIPTION OF THE PREFERRED EMBODIMENT

A glass capillary tube 1 having a length of about 100 mm and a volume of about 100 microliters, is closed at each end by means of a stopper of epoxy resin 2. It may be suitable to provide a notch, groove or scratch 3 at each end of the capillary tube to make it easier to open the glass. On the interior wall of the glass is a coating 4 of small crystals or amorphous particles of the reducing agent, for example sodium dithionite, the optional buffer and the optional anti-coagulating agent.

The following examples illustrate the invention:

EXAMPLE 1

Sodium dithionite and Tris were ground separately in a ball grinder for 8–12 hours. The ground powders were mixed in the ratio of 31 parts by weight of sodium dithionite to 22 parts by weight of Tris, and the final powder was suspended in dichloromethane ($CH_2Cl_2$) in the ratio of 1 g powder to 6 ml of dichloromethane. The resulting suspension was continuously stirred to prevent sedimentation. This operation and all the subsequent operations in the preparation procedure were performed under an inert atmosphere, as, otherwise, sodium dithionite would be decomposed within a few minutes in the presence of oxygen or water vapor. A capillary tube having a length of 100 mm and an interior volume of about 100 microliters was dipped about 1 cm into the suspension and was thereafter lifted up from the suspension, and the resulting liquid string was suctioned to the other end of the tube. Through this, the dichloromethane evaporated, and a substantially uniform coating was formed on the interior wall of the tube. Thereafter, the tube was closed at both ends with a material impermeable to oxygen and water, for example epoxy resin, and was ready for shipping.

EXAMPLE 2

(a) The same procedure as in Example 1 was followed with the exception that additionally 11.13 mg of heparin was added per 6 ml of $CH_2Cl_2$. When using 10 microliters suspension per capillary tube, the prepared tubes each contained about 19 micrograms of heparin, which is about 20 times the amount necessary.

(b) Instead of heparin, also other anticoagulants may be used, for example trisodium citrate, ethylenediaminetetraacetic acid or especially the disodium salt thereof, sodium fluoride or succinic acid monolithium, monosodium or monopotassium salt. The amounts of these anticoagulating agents used are:

|  | Per 6 ml $CH_2Cl_2$ | In the final capillary tube |
|---|---|---|
| Trisodium citrate | 286 mg | about 500 micrograms |
| ethylenediamine-tetraacetic acid-disodium salt | 48 mg | about 80 micrograms |
| sodium fluoride | 600 mg | about 1000 micrograms |
| oxalic salt monolithium, monosodium or monopotassium salt | 120 mg | about 200 micrograms |

EXAMPLE 3

A determination of carbon monoxide hemoglobin using a capillary tube prepared according to Example 2(a) is performed as follows:

(1) The tube is cut at both ends to remove the stopper material.
(2) The blood sample is transferred to the tube which is filled up completely. Suitably, the blood sample can simply be withdrawn directly from the patient into the capillary tube in the well-known manner.
(3) A small piece of steel wire serving as a magnet stirrer is put into the capillary tube, whereafter the capillary tube is stoppered with plasticine or a similar material.
(4) The steel wire piece in the capillary tube is moved by means of a magnet so that the sample is thoroughly mixed, whereafter it is allowed to stand for about 5–8 minutes.
(5) The tube is cut at both ends and the sample is transferred anaerobically to a suitable photometer in which the measurement is performed.

What is claimed is:

1. A method of deoxygenating a blood sample, comprising breaking the seal of an air-tightly sealed capillary tube containing a dry reducing agent for the oxygen content of the blood, introducing the blood sample into the unsealed capillary tube containing said dry reducing agent, and allowing the action of the reducing agent on the blood sample.

2. A method as claimed in claim 1 wherein the capillary tube is filled up completely with the blood sample and is thereafter sealed at both ends, and the blood sample and the reducing agent are mixed with each other in the capillary tube by means of a ferromagnetic body placed in the capillary tube and moved by means of a magnet outside the capillary tube.

3. A method according to claim 1, wherein said blood sample is whole blood.

4. A method according to claim 1, wherein the carbon monoxide hemoglobin content of said blood sample is determined after said reducing agent acts upon said blood sample.

5. A capillary tube for use in a method for deoxygenating blood, comprising an air-tightly sealed capillary tube containing a dry reducing agent for reducing the oxygen content of blood in a sufficient amount for reducing the oxygen content of the volume of blood which can be contained in the capillary tube.

6. A capillary tube as claimed in claim 5 wherein the reducing agent is present as a solid material on the interior wall of the capillary tube.

7. A capillary tube as claimed in claim 5 wherein the reducing agent is sodium dithionite.

8. A capillary tube as claimed in claim 5 which additionally contains a pH buffer.

9. A capillary tube as claimed in claim 5 which contains a mixture of a reducing agent, a pH buffer and an anticoagulating agent present as a solid composition on the interior wall of the capillary tube.

10. A capillary tube according to claim 5, wherein said blood is whole blood.

11. A capillary tube as claimed in claim 5 which additionally contains an anticoagulating agent.

12. A capillary tube as claimed in claim 11 wherein the anticoagulating agent is heparin, trisodium citrate, disodium salt of ethylenediamine-tetraacetic acid, sodium fluoride or an alkali metal oxalate.

* * * * *